United States Patent
Laufer et al.

(10) Patent No.: US 8,092,474 B2
(45) Date of Patent: Jan. 10, 2012

(54) METHODS AND DEVICES FOR PLACEMENT OF AN INTRA-ABDOMINAL OR INTRA-THORACIC APPLIANCE THROUGH A NATURAL BODY ORIFICE

(75) Inventors: Michael D. Laufer, Menlo Park, CA (US); Amos G. Cruz, Bellingham, MA (US); Thomas R. Cygan, Marlborough, MA (US); Jennifer Almy, Auburndale, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 869 days.

(21) Appl. No.: 12/107,717

(22) Filed: Apr. 22, 2008

(65) Prior Publication Data

US 2009/0005797 A1 Jan. 1, 2009

Related U.S. Application Data

(60) Provisional application No. 60/931,243, filed on May 21, 2007.

(51) Int. Cl.
*A61B 17/08* (2006.01)
*A61F 2/00* (2006.01)
*A61F 13/00* (2006.01)

(52) U.S. Cl. ............... 606/157; 606/151; 600/37
(58) Field of Classification Search ............ 600/37; 606/151, 157, 201–203
See application file for complete search history.

(56) References Cited

U.S. PATENT DOCUMENTS

| | | | |
|---|---|---|---|
| 5,074,868 A * | 12/1991 | Kuzmak | 606/157 |
| 5,159,446 A * | 10/1992 | Hibino et al. | 348/65 |
| 5,449,368 A * | 9/1995 | Kuzmak | 606/157 |
| 6,494,888 B1 | 12/2002 | Laufer et al. | |
| 6,572,629 B2 * | 6/2003 | Kalloo et al. | 606/151 |
| 6,663,639 B1 | 12/2003 | Laufer et al. | |
| 6,676,674 B1 * | 1/2004 | Dudai | 606/151 |
| 6,966,875 B1 * | 11/2005 | Longobardi | 600/31 |
| 7,841,347 B2 | 11/2010 | Sonnenschein et al. | |
| 2001/0049497 A1 * | 12/2001 | Kalloo et al. | 604/164.01 |
| 2002/0022851 A1 * | 2/2002 | Kalloo et al. | 606/151 |
| 2002/0169464 A1 * | 11/2002 | Latour | 606/151 |
| 2003/0208212 A1 * | 11/2003 | Cigaina | 606/151 |
| 2004/0102804 A1 * | 5/2004 | Chin | 606/190 |
| 2005/0075652 A1 * | 4/2005 | Byrum et al. | 606/139 |
| 2005/0261712 A1 * | 11/2005 | Balbierz et al. | 606/153 |
| 2005/0277963 A1 * | 12/2005 | Fields | 606/153 |
| 2005/0283235 A1 | 12/2005 | Kugler et al. | |
| 2006/0178564 A1 * | 8/2006 | Jones et al. | 600/159 |
| 2006/0241653 A1 * | 10/2006 | Jones et al. | 606/125 |
| 2006/0252983 A1 * | 11/2006 | Lembo et al. | 600/37 |
| 2007/0015956 A1 * | 1/2007 | Crawford et al. | 600/37 |
| 2007/0038239 A1 * | 2/2007 | Ritchie | 606/192 |
| 2007/0218083 A1 * | 9/2007 | Brooks | 424/239.1 |
| 2008/0208216 A1 * | 8/2008 | Cerier | 606/139 |
| 2008/0319435 A1 * | 12/2008 | Rioux et al. | 606/33 |
| 2009/0018391 A1 | 1/2009 | Laufer et al. | |

FOREIGN PATENT DOCUMENTS

WO  WO-2007064906 A2  6/2007

* cited by examiner

*Primary Examiner* — Corrine M McDermott
*Assistant Examiner* — Dianne Dornbusch
(74) *Attorney, Agent, or Firm* — Nutter McClennen & Fish LLP

(57) ABSTRACT

Natural orifice transenteric surgical methods and devices for placing a band or other appliance around a hollow bodily organ such as the stomach. In one alternative embodiment, such a band is placed in order to reduce the inner volume of the stomach.

28 Claims, 14 Drawing Sheets

US 8,092,474 B2

METHODS AND DEVICES FOR PLACEMENT OF AN INTRA-ABDOMINAL OR INTRA-THORACIC APPLIANCE THROUGH A NATURAL BODY ORIFICE

CROSS-REFERENCE TO RELATED APPLICATION

This application claims the benefit of Provisional Patent Application No. 60/931,243, filed May 21, 2007, which is incorporated by reference herein in its entirety.

TECHNICAL FIELD OF THE INVENTION

Generally, the present invention is related to trans-luminal surgical devices and methods. More particularly, the devices and methods herein described provide for gastric restriction and volume reduction by the placement of an appliance on the outer surface of the stomach from access obtained via the inside of the stomach. These devices may also be used to place an appliance on other hollow bodily conduits or organs.

BACKGROUND OF THE FIELD OF THE INVENTION

Laparoscopic surgery has greatly reduced the size and scope of incisions made in a patient and resulted in reduced morbidity and mortality rates. However, even with the reductions in the size and extent of incisions as a result of laparoscopic surgery, complications in and during surgical procedures remain. A technique that is developing to further reduce surgical complications is to work through a natural orifice such as the mouth, to access the stomach, where a hole is made through the stomach wall, to gain access to the inside of the abdominal space outside of the stomach. This NOTES approach, or natural orifice transenteric surgery, allows scarless surgical procedures with faster recovery, fewer complications, and less pain.

Stomach tissue often needs surgical treatment to treat fistulas and to close trans-gastric incisions to stop stomach fluids from leaking from the stomach to surrounding tissue and to stop infectious matter from spreading from or to the stomach tissue. Other stomach treatments include stomach reduction procedures for obese patients. Traditionally, physicians have placed devices laparoscopically on the external surface of the gastric wall to create a restricted stomach capacity. Another traditional procedure for stomach reduction includes a laparoscopic procedure in which surgeons protrude into the abdomen from the exterior of the patient and staple the stomach into a smaller volume. This restriction creates a pouch inside the stomach which fills quickly when food is ingested and assists in generating a sensation of being full. However, these procedures have drawbacks such as complications from port punctures of the stomach, large incisions, substantial recovery time, expense, lost productive work time, infection, and the like.

However, the incision required by the current surgical procedures including laparoscopy, include a morbidity and mortality rate that can be reduced by reducing or eliminating the need for an incision by approaching the surgical site through endoluminal procedures.

SUMMARY OF THE INVENTION

Embodiments of the invention provide devices and methods for placing a band or other appliance around a hollow bodily organ such as the stomach without any skin incisions. In one alternative, a gastroscope is placed into the stomach and a hole is made through the stomach wall. This provides a route outside of the stomach. Another similar hole is made on the other side of the stomach, about opposite to the first hole. The band is passed out of one hole and the passed end is retrieved by a retractor that has been passed out of the other hole and has been advanced around the outside of the stomach. When the band has been docked or otherwise connected to the retractor, the band is drawn back into the hole which the retractor was passed through. The process is then repeated by passing the retractor in the other direction around the stomach and retracting the other end of the band into the transgastric hole. The ends of the band are then attached by one of a variety of means, and the band that now runs around the outside of the stomach, is tightened around the stomach. The gastric holes are closed by suturing or other fixation device. The band may be included within the closure, which restricts the subsequent movement or slippage of the band over time.

Embodiments of the present invention include a method of placing and/or affixing an appliance on the wall surface of a hollow bodily organ by moving through the wall to access the other surface of the wall of the organ. The hollow bodily organ may be one from the list of: the stomach, the intestine, the heart, the airway, the vein, the artery, the esophagus, the aorta, the renal artery. The surface may the inner surface or the outer surface. In exemplary embodiments, moving through the organ wall may comprise piercing, cutting, injecting and/or burning through the wall to create on opening passage to the other surface of the wall.

The appliance or device as implanted may be circumferential around the hollow bodily organ and it may, alternatively, be in its placed configuration upon placement or reconfigured after placement. Moving through the wall may occur at the location of the placing an appliance on the wall surface. Affixing of the appliance or device may include at least one of the following actions: suturing, stapling, gluing, affixing, tissue-welding, encapsulating, marcupializing, engulfing with tissue, tacking, tethering;

In an alternative embodiment of the invention, a method of placing an appliance on the outer wall surface of a hollow bodily organ comprises entering the hollow bodily organ, making a passageway through the wall of the hollow bodily organ, placing a guide wire through the passageway to the outside of the hollow bodily organ, placing a conduit over or adjacent the guide wire through the wall and out of the hollow bodily organ, directing the guide wire around the outside wall of the hollow bodily organ, re-entering the hollow bodily organ through the passageway previously made, sliding the appliance onto the guide wire such that it follows the path of the guide wire around the hollow bodily organ, adjusting the circumference of the hollow bodily organ by shortening the appliance length around the hollow bodily organ, affixing the appliance in place. The position of the guide wire or tube on the outside of the organ may be assessed by the visibility of light coming from a light source on the guide wire or tube.

In a further alternative, the step of directing the guide wire around the outside wall of the hollow bodily organ may comprise use of a curved conduit as a guide. In another alternative, the step of directing the guide wire around the outside wall of the hollow bodily organ may comprise moving through the wall of the hollow bodily organ at a position only partially around the circumference of the hollow bodily organ, entering the stomach through the wall through a new passageway there created, placing another guide wire through the entrance hole of the first guide wire through the wall and out of the stomach, directing the guide wire further around the hollow bodily organ, re-entering the hollow bodily organ at another position through a new passageway there created that is further around the circumference of the stomach, attaching the second end of the first wire with the first end of the second wire and pulling the junction through the passage through the wall, repeating this process until the organ is completely surrounded by a guide wire with only two ends coming into the hollow bodily organ.

The making of a passageway through the wall of the hollow bodily organ may optionally comprise use of a needle knife to make the passageway. Alternatively, making a passageway through the wall of the hollow bodily organ may comprise energizing the guide wire with radiofrequency energy where the tip and source connection of the guide wire are electrically conductive.

In some embodiments, the step of attaching the second end of the first wire with the first end of the second wire may be done with magnets. In other embodiments, the attaching of the second end of the first wire with the first end of the second wire may be done a threaded connector or, with mechanical means such as twisting, crimping, tying, welding, splicing. The attachment may be done inside the body or outside.

In another alternative embodiment, directing the guide wire around the outside wall of the hollow bodily organ may include vibrating the wire axially, rotationally, and/or transaxially. Alternatively, such directing may include displacing tissue anterior to and/or around the guide wire by increasing the effective diameter of the guide wire. Increasing the effective diameter of the guide wire may comprise inflating a balloon, moving an inner member of the guide wire relative to an outer member of the guide wire to pivot a dissecting member, moving an inner member of the guide wire relative to an outer member of the guide wire to expand the tip diameter of the guide wire.

Alternatively, directing the guide wire may comprise moving an inner member of the conduit relative to another member of the conduit so as to flex the tip of the conduit, or rotating the conduit relative to the passageway through the wall of the hollow bodily organ.

In yet a further alternative embodiment of the present invention, a method of placing an appliance on the outer wall surface of a hollow bodily organ may comprise entering the hollow bodily organ, making a passageway through the wall of the hollow bodily organ, placing the appliance through the passageway to the outside of the hollow bodily organ, placing a conduit over or adjacent the appliance through the wall and out of the hollow bodily organ, directing the appliance around the outside wall of the hollow bodily organ, re-entering the hollow bodily organ through the passageway previously made, adjusting the circumference of the hollow bodily organ by shortening the appliance length around the hollow bodily organ, affixing the appliance in place.

DETAILED DESCRIPTION OF THE INVENTION

Figure 1:
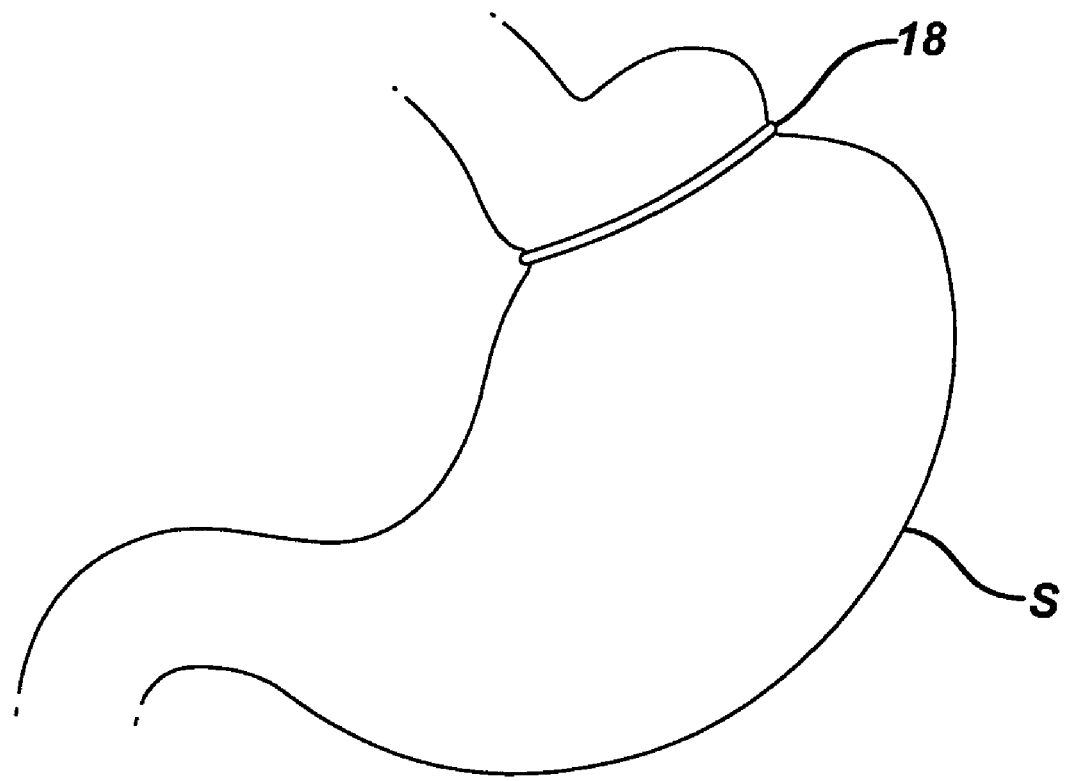
FIG. 1 illustrates an example of a hollow body organ, in this case a stomach, with a device according to an embodiment of the present invention deployed thereon.

Embodiments of the present invention include an implant device configured to be implanted onto a lumen of a hollow bodily organ or conduit including the stomach, the intestine, the heart, the airway, the vein, the artery, the esophagus, the aorta, and/or the renal artery without creating an incision outside the body, wherein the implant can be configured and/or adjusted to constrict or reduce the stomach or other hollow bodily organ or conduit. An exemplary embodiment is shown in FIG. 1, wherein a band 18 is deployed around a patients stomach S. Embodiments of the invention further include a method for less invasively deploying such devices through natural body orifices.

Exemplary method steps includes the steps of placing an instrument such as an endoscope into the stomach or other organ or conduit through the mouth or other natural orifice, making a hole through the stomach or hollow organ or conduit wall, directing a flexible wire or tube at least partially around the outside of the stomach and re-entering the stomach at or near the point of the original exit from the stomach. Suitable endoscopic devices including tissue manipulating functionality are disclosed, for example, in U.S. Pat. Nos. 6,494,888 and 6,663,639, which are incorporated by reference in there entirety herein. The hole can be made by cutting, piercing, burning with RF energy directed into the tissue through a conductive tip on the wire or needle knife, or similar method know by those practitioners of the art.

Figure 2A:
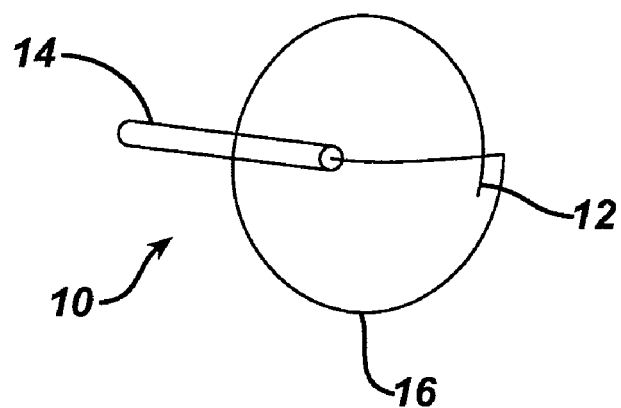
FIGS. 2A and B illustrate an embodiment of a guide wire according to the present invention.
Figure 2B:
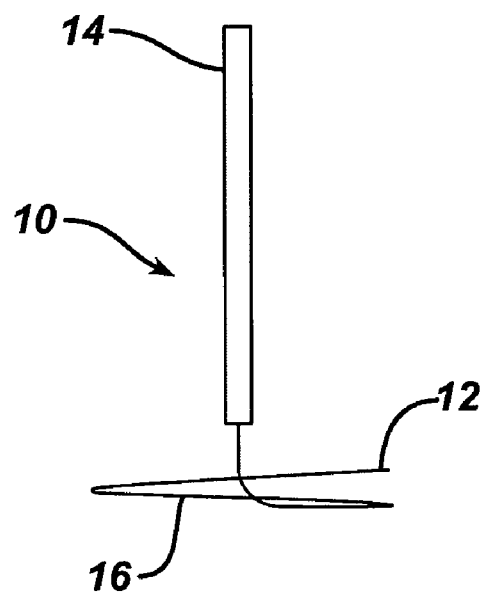
Figure 4:
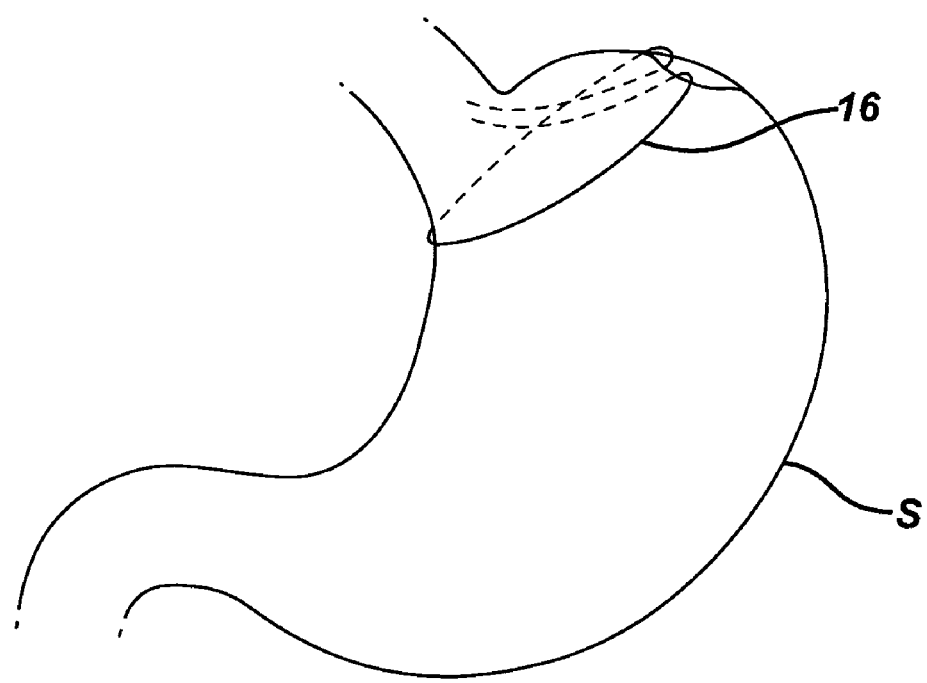
FIG. 4 illustrates placement of a guide wire according to an embodiment of the invention in a patient's stomach.

Referring to FIGS. 2A and B, an exemplary embodiment of a guide wire device 10 is shown. Guide wire device 10 has a tip 12 that may be energized with RF energy, sharpened or otherwise configured to puncture through the wall of a hollow bodily organ from the inside. By manipulating handle 14, the wire 16 of the guide wire device 10 is moved through and outside the wall of the organ around the organ as shown in FIG. 4. Throughout such a procedure, the user manipulable, proximal end of the handle 14 remains outside of the mouth or other natural body orifice, for example through an endoscopic device as mentioned above.

Figure 3A:
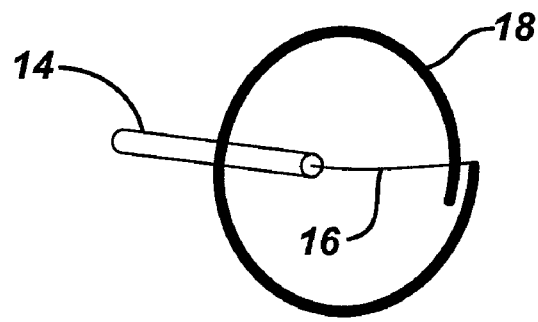
FIGS. 3A and B illustrate a band placed over a guide wire according to one embodiment of the present invention.
Figure 3B:
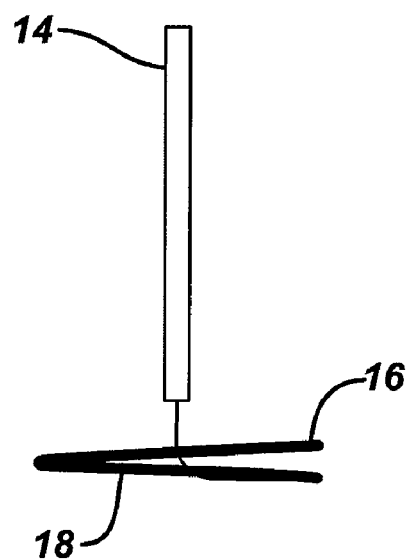

Once the guide wire 16 is placed around the hollow body organ, a restricting band 18 may be advanced there over as shown in FIGS. 3A and B. Alternatively, a guide tube first may be extended over the guide wire and the restricting band deployed either inside or outside the guide tube.

Figure 6:
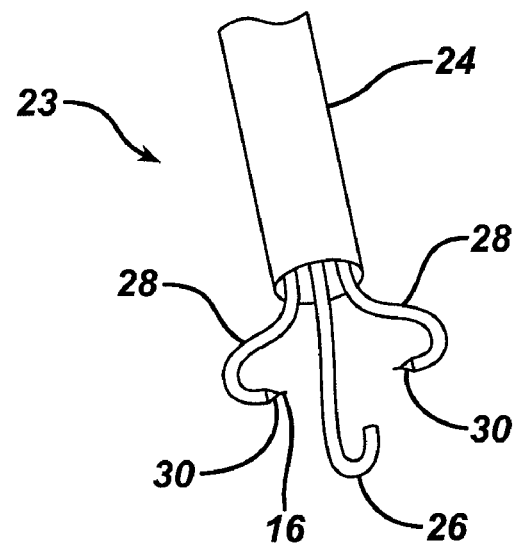
FIG. 6 illustrates a distal end of a device according to an embodiment of the present invention for deploying a guide wire and restricting band.

An exemplary device 23 for placement of guide wire 16 and appliance 18 is illustrated in FIG. 6. As shown, outer tube 24 is used to deliver endoscope 26 and manipulable arms 28 through the esophagus and pyloric valve into the stomach. Manipulable arms 28 may include tissue piercing elements 30 at each distal end and may be hollow to permit delivery of the guide wire 16. As one possible alternative, such a device may be configured largely as described in the previously incorporated '888 or '639 patents.

Using device 23, appropriate locations on the organ wall can be visualized with endoscope 26 and pierced by the tissue piercing elements on manipulable arms 28. Guide wire 16 can then be advance through the organ wall and around the outer surface of the organ. Means for directing the guide wire are discussed below. Upon return to the exit opening or a secondary opening created by piercing elements 30, guide wire 16 may be recaptured by manipulable arms 28, or an alternative device, such as a grasper arm inserted through tube 24 can be used for this purpose. With the end of the guide wire 16 recaptured, it can be returned external to the hollow organ (and patient) and the appliance 18 guided into place therewith.

Figure 7A:
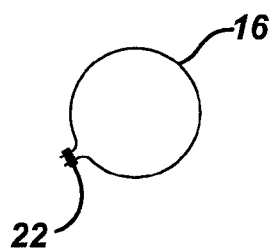
FIGS. 7A and 7B illustrate alternative embodiments of guide elements and securing elements according to the present invention.
Figure 7B:
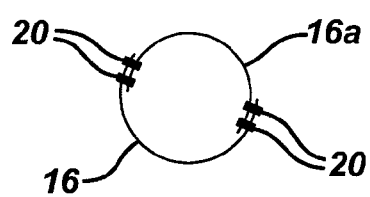

In another embodiment of the present invention, the wire 16 or guide tube can be made to exit the stomach and reenter the stomach at points partially around the outside of the stomach. Manipulable arms 28 and piercing elements 30 provide an exemplary embodiment for accomplishing such a procedural alternative. Another wire or guide tube 16a is then used to reenter the previous exit hole or entry hole where it is then directed at least partially around the stomach. Two close ends of the two wires or tubes or one wire and one tube are then joined. Such joining may be accomplished, for example by magnets 20 attached to each wire end or by twisting or clipping the ends together, or by placing the wire inside of the nearby tube end and crimping them together with one or more fasteners 22 as shown in FIGS. 7A and B. The wire or tube may be pulled so that the junction of the wires and/or tubes is pulled out of the stomach and a single wire or tube goes all the way around the stomach. This wire or tube is then used to place an appliance around the stomach over or through the tube such that the wire or tube is used as a rail-like or tunnel-like guide for placement of the appliance.

The guide wire or tube may encounter resistance or encounter tissue through which it must pass. In that case, the wire or tube may be rotated, vibrated axially at audible or sub-ultrasonic frequencies, to act similarly to a jack-hammer but at a much smaller scale, or may be alternately flexed in one direction and then another at some frequency in order to make passage possible.

Figure 5A:
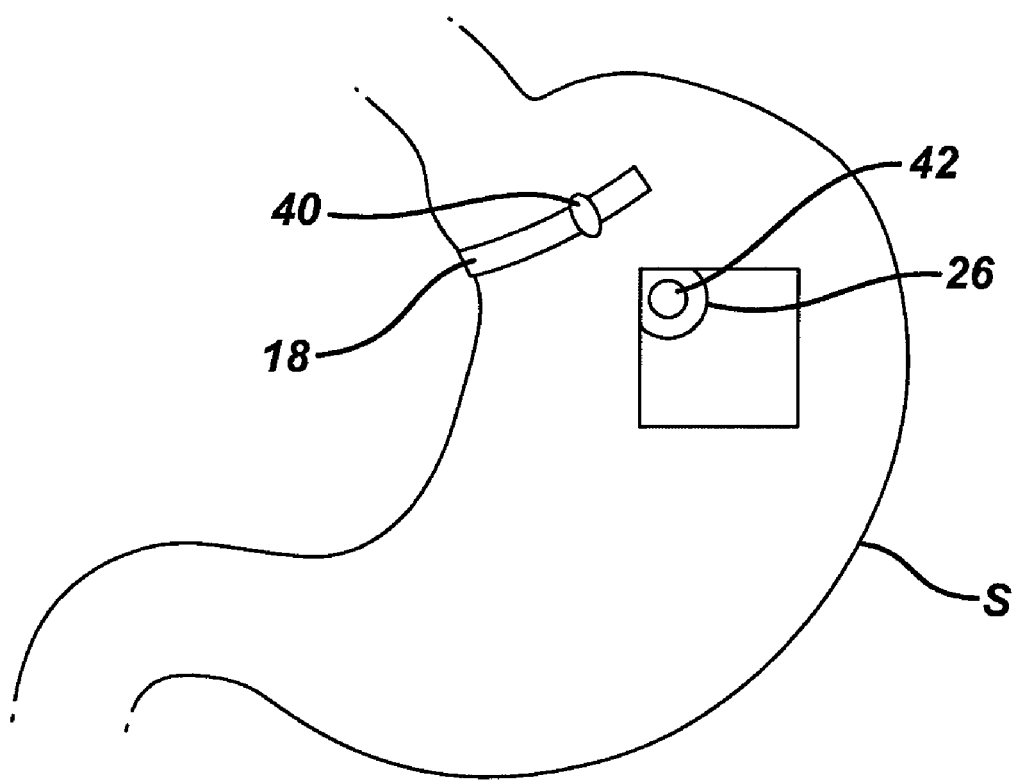
FIG. 5A is a side view of a patient's stomach, with a square shaped cut-away to reveal the interior, illustrating a further embodiment of the invention including a band and magnets positioned on the outside of a patient's stomach.
Figure 5B:
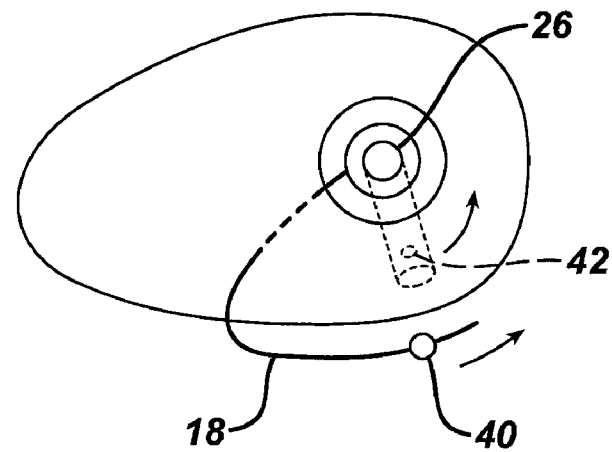
FIG. 5B illustrates a cross-section of a patient's stomach including an embodiment of the invention as shown in FIG. 5A.

Alternatively, as shown in FIGS. 5A and B, the guide element may be magnetically driven without additional openings through the organ wall. Here, guide element 16 or band 18 is provided with a magnetic element 40 at or near the advancing end. In this view, a square cut-away of the wall of the stomach S is shown to reveal the endoscope 26 within the interior of the stomach. Using complementary magnets 42 placed on the endoscope 26, or other manipulable device, the band may be driven around the organ by rotating the endoscope. The arrangement is also illustrated in the cross-sectional top view of FIG. 5B.

The guide wire or tube may also be configured with a tip that allows axial expansion for passage through tissue. This dissection may be accomplished through expanding a balloon on the guide wire or tube in order to create a space to loosen the tissue, deflating the balloon and advancing the guise wire or tube, re-expanding the balloon, and repeating as often as necessary to accomplish passage. Alternatively, the tip of the guide wire or tube may have a scissor-like member, where the method entails opening and closing while pushing the guide wire or tube, in order to accomplish passage.

In another embodiment, the guide wire or tube may have a light source to allow it to be seen through the stomach wall as it is passing around the stomach, the method involving directing and redirecting the guide wire or tube based on seeing the light contained on the guide wire or tube through the wall of the organ.

In one embodiment, the appliance has channels through which the wire or tube are threaded. The appliance is then directed around the hollow bodily organ or conduit until it is positioned around the stomach or bodily organ by pushing or pulling it around the stomach, either with the wire as the puller or pusher, or with a pusher or puller that is also placed over or through the guide wire or tube. The ends of the appliance may be connected directly or by threading one end through the other end to form a loop or by other similar method such as loop and hook fastener, snaps, magnets, tying the ends together, suturing the ends together or other method know to practitioners of the art. The length of the appliance in part determines the amount of constriction of the hollow organ around which it is placed. The amount of tightening determines the amount of constriction.

In another embodiment, the appliance is placed around the organ directly without the need for an additional guide wire or tube, which is integrated into the appliance.

In another embodiment, the appliance may be adjusted after placement by injecting a fluid into the appliance. This injection can be accomplished with a needle directed through the stomach wall directly into the appliance or into a reservoir attached to the appliance. Alternatively, it can also be adjusted by applying energy through capacitive coupling between a coil on the appliance and a coil inside the organ, said energy being used to move a piezo-actuator or motor that contracts the length of the band.

In another embodiment, the amount of constriction of the hollow bodily organ can be varied after placement of the band by allowing the band to swell or shrink through absorbing or losing fluid from its environment. A hydrogel or other polymeric or fibrous material will absorb fluid when the appliance is loose, and will lose fluid when the appliance is tight, as a sponge does when it is squeezed.

The appliance may be fixed in place on the organ by suturing, stapling, folding tissue over it and affixing the tissue by suturing, stapling, or using a Plicator® such as from NDO Surgical, INC. in what may be described as marcupialization, tacking, gluing or tethering.

Means for docking or connecting the band to the retractor to pull the band around the stomach include hook and loop devices such as Velcro, magnets and electromagnets, mechanical graspers, hooks, barbs and adhesives. A spiral cork-screw-like device may also be used as a docking grasper. The band or appliance can be adjusted my means of a zip-tie like mechanism, a ratchet system, a ferrite-activated ratcheting system or a motor that effectively shortens the band.

The ratcheting system may be activate after implantation by means of an external magnet causing the ferrites to alter their configuration, or alternatively by using a motor or piezo to effectively shorten the band length. The activation and power may be provided without the need for injections or incisions by coupling the power source with the implanted band through the skin by means of induction coils or magnetic flux through the skin. The effector or power supply may be external to the patient or on a device within the stomach such as an endoscope or other device placed into the stomach though the mouth and esophagus.

Should the anatomic variations or requirements of a given patient require additional access, a single percutaneous gastrostomy may be done were a hole is made directly from the abdominal wall into the stomach. Instruments may be placed through this access port to accomplish the procedure.

Figure 8A:
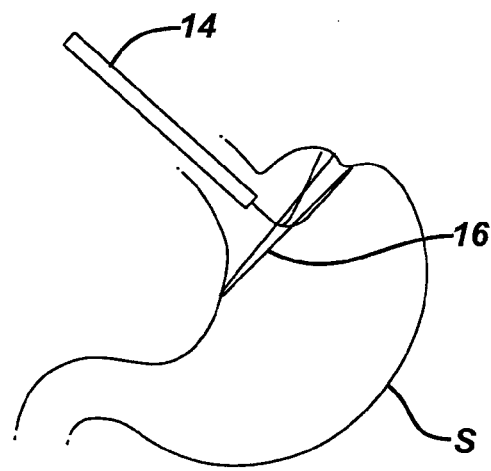
FIGS. 8A and 8B illustrate an alternative guide element and placement on a hollow body organ.
Figure 8B:
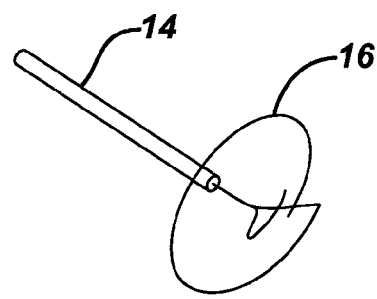

As shown in FIGS. 8A and 8B, wire 16 may be formed with two segments pushing against th stomach wall S and the leading tip of the wire puling on the wall.

Figure 9:
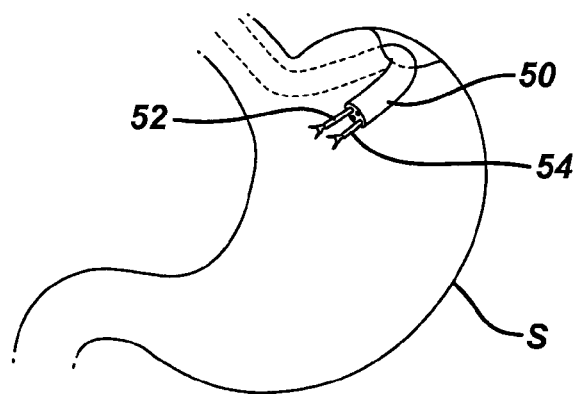
FIG. 9 illustrates a further alternative embodiment of the present invention.

In another alternative embodiment, shown in FIG. 9, the guide element 50 may be formed with a scope or as a scope like device that can crawl around the stomach S to pass or leave the guide element 16 in place. Forceps like graspers 52 and 54, manipulable from outside the patient's body can facilitate this procedure.

Figure 10A:
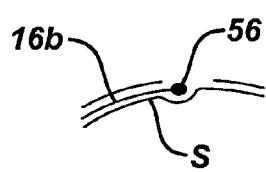
FIGS. 10A and 10B illustrate another alternative embodiment of a guide element and placement according to the present invention.
Figure 10B:
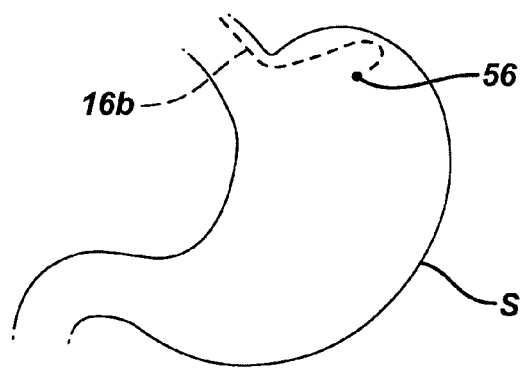

FIGS. 10A and 10B show a guide wire 16b that includes a distal bump tip 56. In this alternative embodiment, the bump tip 56 can be advanced around the stomach S from the inside, pushed with a peristalsis like motion.

Figure 11:
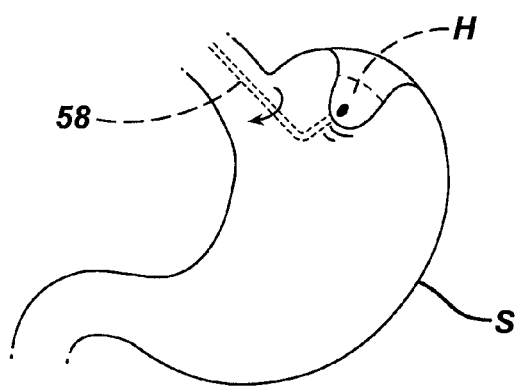
FIGS. 11 and 12 illustrate another alternative embodiment of the present invention.
Figure 12:
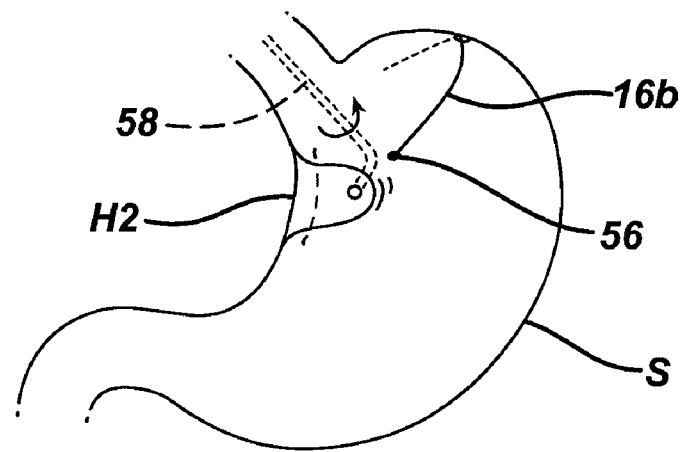

Placement of an appliance around the stomach S through a gastronomy hole H is shown as a further alternative in FIGS. 11 and 12. Here, the gastronomy hole H is moved using manipulator 58 (like when wrapping the fundus in a nissen fundoplication). Wire 16b is then left outside the stomach S. Subsequently, as in FIG. 12, a second gastronomy hole is moved using element 58 in similar fashion to retrieve retrieve wire 16b.

Figure 13:
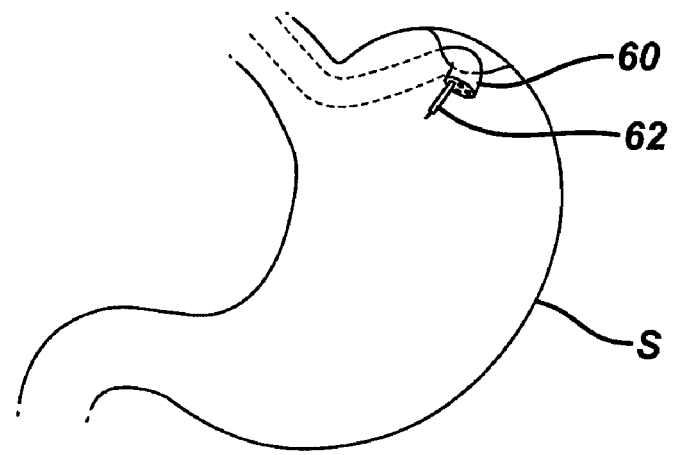
FIG. 13 illustrates yet another alternative embodiment including a steerable guide element and scope.

FIG. 13 illustrates another alternative embodiment wherein a steerable wire 62 is pushed around the stomach utilizing scope 60.

Figure 14A:
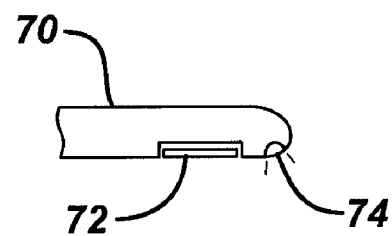
FIGS. 14A and 14B illustrate a steerable guide element with illumination source according to a further alternative embodiment of the present invention.
Figure 14B:
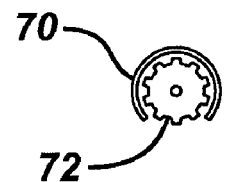

An embodiment of a steerable wire 70 is shown in FIGS. 14A and 14B. In this embodiment, inner member 72 is rotated to the left or right to steer the guide wire 70. The distal tip can be equipped with a light source 74 to facilitate visualization directly with a scope or indirectly through the stomach wall.

Figure 15A:
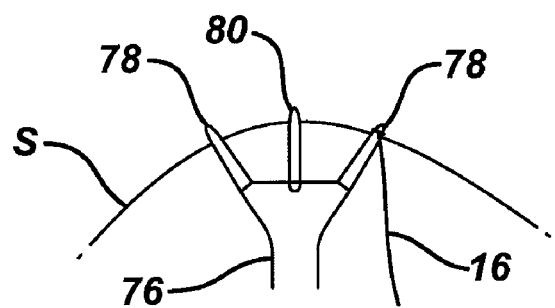
FIGS. 15A and 15B illustrate another embodiment including piercing arms for grasping and deploying a guide element.
Figure 15B:
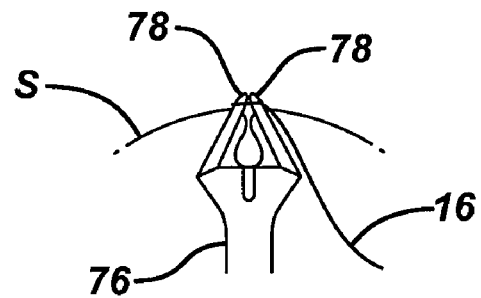
Figure 16A:
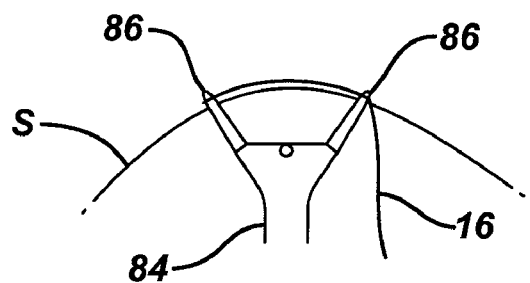
FIGS. 16A, B, and C disclose yet another alternative embodiment with grasping arms for deployment of the guide element according to the present invention.
Figure 16B:
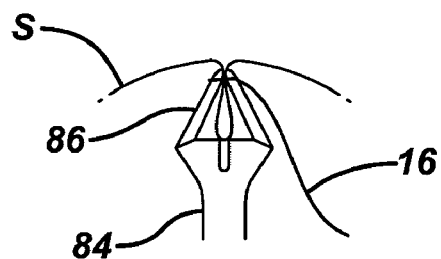
Figure 16C:
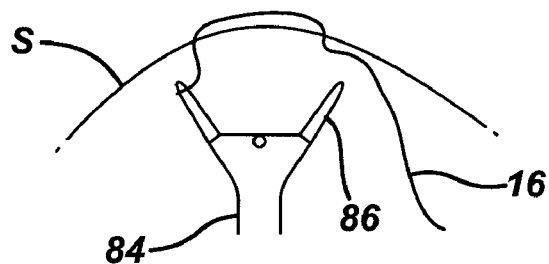

In yet another embodiment, a manipulable member 76 may be deployed through a delivery tube into the stomach S with tissue piercing arms 78, 80 at the distal end. Such arms also may include graspers for manipulating the wire 16. As shown in FIG. 15B, once the stomach wall is pierced, the wire is passed from one arm to another. A series of these actions are performed to completely encircle the stomach to the extent desired. In a similar alternative, rather than the grasping arms piercing, the wire itself may be used for piercing. Such an embodiment is shown in FIGS. 16A-C. Once again, grasping arms 86 on manipulable member 84 pass the wire 16 through the stomach wall S in a series of steps around the stomach circumference as shown.

Figure 17:
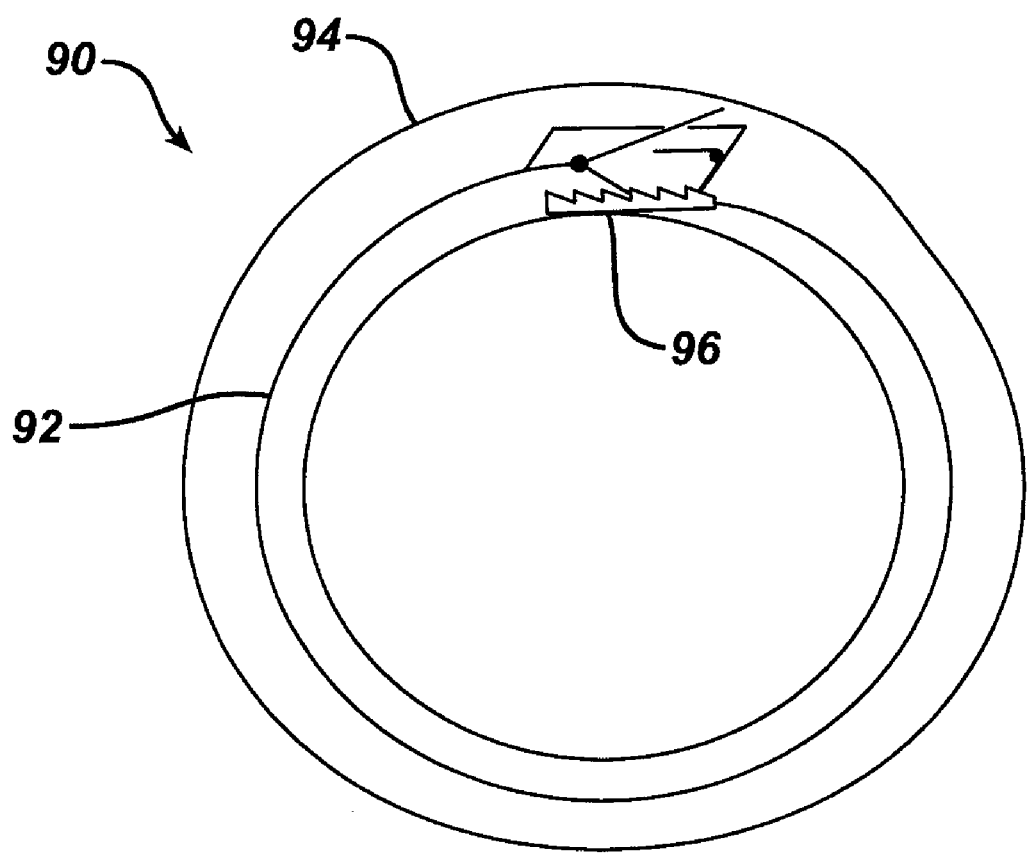
FIGS. 17-22 each illustrate alternative embodiments of an adjustable appliance for placement around the outside of a hollow bodily organ according to the present invention.
Figure 18:
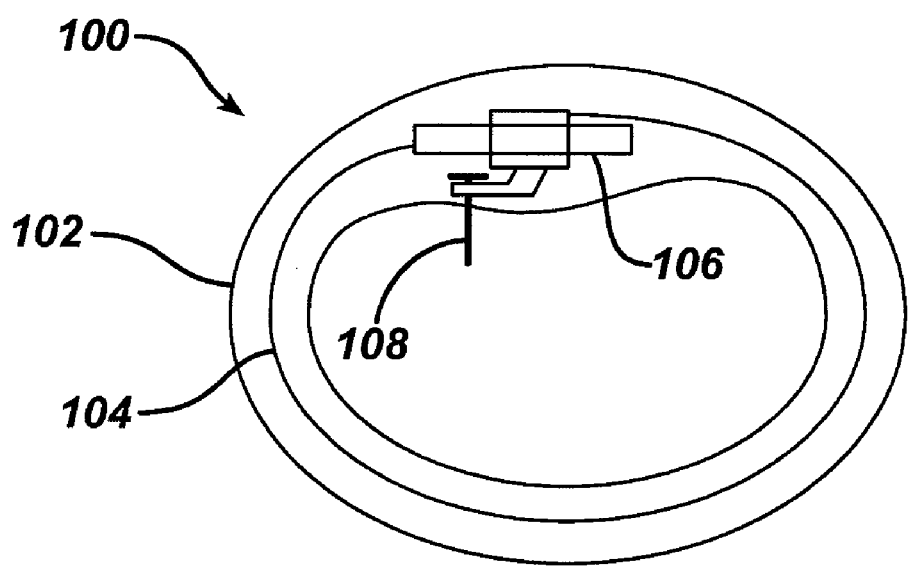

Various alternative appliances and means for adjusting such appliances are also part of the present invention. For example, appliance 90 as shown in FIG. 17 includes an adjustable ratchet 96. An internal band 92 attached to the ratchet may be covered with a compliant covering 94. In use the adjustable band 90 is dilated to size. When dilated to maximum diameter, the ratchet mechanism 96 allows the band 90 to collapse to the minimum diameter and re-dilating can be performed. FIG. 18 shows a similar alternative embodiment of adjustable band 100. Here, the band 100 is adjustable with a carjack-like mechanism 106 actuated by a temporary T-tag 108. Again, an inner member 104 is surrounded by a compliant and protective cover member 102.

Figure 19:
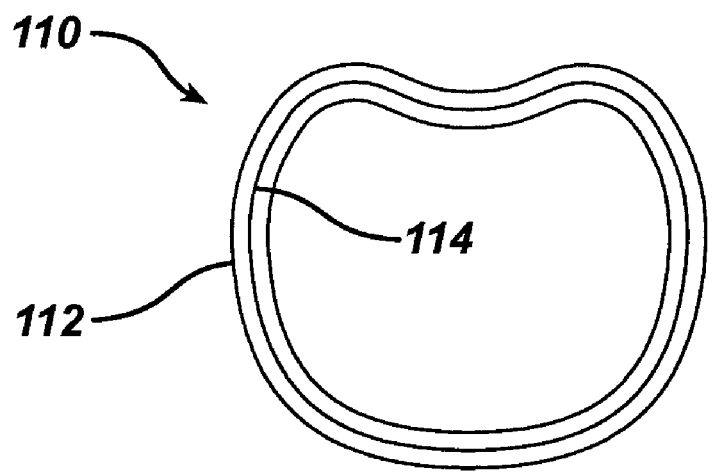
Figure 20:
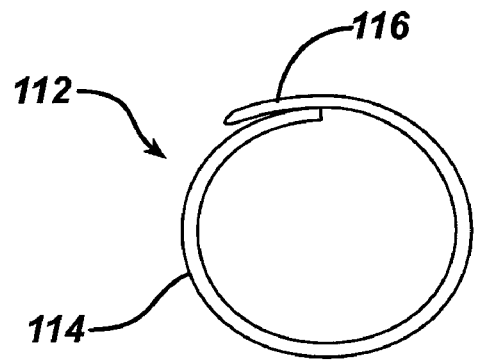
Figure 21:
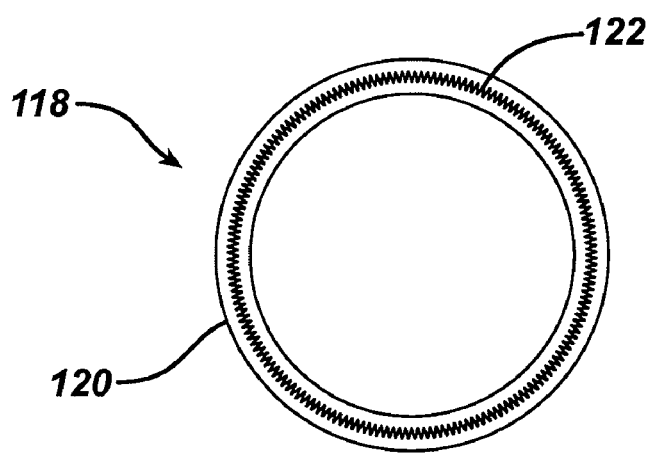

A further alternative adjustable appliance 110, includes a malleable core 114 surrounded by a compliant cover 112 as shown in FIG. 19. Sizing may be decreased by bending with a manipulation element such as remote actuated forceps. Other alternative adjustment means include a band 112 with a flexible member 114 having an overlapping fastener region 116 in the form of a key ring structure as shown in FIG. 20. Also, a spring biased appliance 118 may include a spring member 122 surrounded by a compliant cover material 120.

Figure 22:
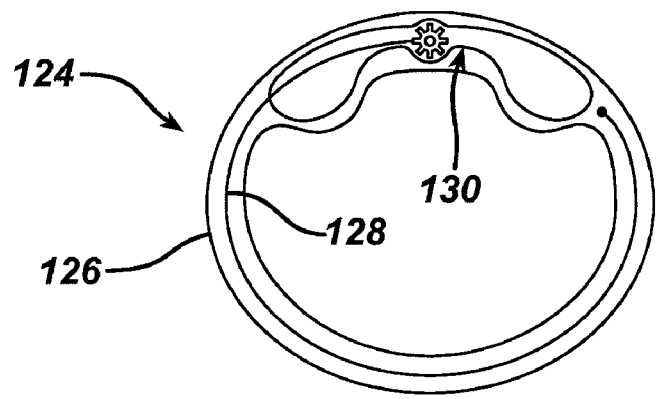

In another embodiment of adjustable appliance 124, a pumping mechanism may be employed as in FIG. 22. Once again, a band member 128 is surrounded by a compliant cover 126. In this embodiment, pump mechanism 130 includes left and right reservoirs. When the reservoir on the right is filled, for example with an endoscopically introduced needle, the pump in the center turns. The pump is linked to the band 128 causing to cinch down as it turns. Filling the opposite reservoir reverses the pump to open band 128.

What is claimed:

1. A method of placing an appliance on a wall surface of a hollow bodily organ, comprising:
    entering the organ through a naturally occurring orifice;
    placing a guide element through an inner wall surface of a wall of the organ to access an outer wall surface of the wall of the organ;
    guiding the appliance with the guide element extending through the appliance to position the appliance on the outer wall surface; and
    removing the guide element and leaving the appliance on the outer wall surface.

2. The method as in claim 1, wherein the hollow bodily organ is one of stomach, intestine, or esophagus.

3. The method as in claim 1, wherein said placing through the wall comprises piercing, cutting, injecting and/or burning through the wall to create an opening passage to the outer wall surface.

4. The method as in claim 1, wherein the appliance is circumferential about the hollow bodily organ.

5. The method as in claim 1, wherein the appliance is initially deployed in its final placed configuration.

6. The method as in claim 1, wherein the appliance is reconfigured after placement.

7. The method as in claim 1, wherein the appliance is affixed to the outer wall surface after guiding into position.

8. The method as in claim 7, wherein said affixing includes at least one of suturing, stapling, gluing, tissue-welding, encapsulating, marcupializing, engulfing with tissue, tacking, and tethering.

9. A method of placing an appliance around an en-the-outer wall surface of a hollow bodily organ, comprising:
    entering the hollow bodily organ;
    making a passageway through a wall of the hollow bodily organ;
    placing a guide element through the passageway to outside the hollow bodily organ;
    directing the guide element around the outer wall surface of the hollow bodily organ;
    re-entering the hollow bodily organ through the passageway previously made;
    after directing the guide element around the outer wall surface, advancing the appliance over the guide element such that the appliance follows a path of the guide element around the outer wall surface of the hollow bodily organ;

adjusting a circumference of the hollow bodily organ by shortening the appliance length around the outer wall surface of the hollow bodily organ; and affixing the appliance in place.

10. The method as in claim 9, wherein a position of the guide element outside of the organ can be assessed by visibility of light coming from a light source on the guide element.

11. The method as in claim 9, wherein directing the guide element around the outer wall surface of the hollow bodily organ comprises using a curved conduit.

12. The method as in claim 9, wherein directing the guide element around the outer wall surface of the hollow bodily organ comprises:

moving through the wall of the hollow bodily organ at a position only partially around the circumference of the hollow bodily organ;

entering the hollow bodily organ through the wall through a new passageway there created;

placing another guide element through an entrance hole of the guide element through the wall and out of the hollow bodily organ;

directing the other guide element further around the hollow bodily organ;

re-entering the hollow bodily organ at another position through a new passageway there created that is further around the circumference of the hollow bodily organ;

attaching a second end of the guide element with a first end of the other guide element and pulling a junction of the second end and the first end through the passageway through the wall; and repeating this process until the organ is completely surrounded by a guide element with only two ends coming into the hollow bodily organ.

13. The method of claim 12, wherein attaching the second end of the guide element with the first end of the other guide element is done with magnets.

14. The method of claim 12, wherein attaching the second end of the guide element with the first end of the other guide element is done with a threaded connector.

15. The method of claim 12, wherein attaching the second end of the guide element with the first end of the other guide element is done with mechanical means including at least one of twisting, crimping, tying, welding, and splicing.

16. The method of claim 12, wherein attaching the second end of the guide element with the first end of the other guide element is done inside the body.

17. The method of claim 12, wherein attaching the second end of the guide element with the first end of the other guide element is done outside of the body.

18. The method of claim 9, wherein making a passageway through the wall of the hollow bodily organ comprises using a needle knife to make the passageway.

19. The method of claim 9, wherein making a passageway through the wall of the hollow bodily organ comprises energizing the guide element with radiofrequency energy where a tip and source connection of the guide element are electrically conductive.

20. The method of claim 9, wherein directing the guide element around the outer wall surface of the hollow bodily organ includes vibrating the guide element axially, rotationally, and/or transaxially.

21. The method of claim 9, wherein directing the guide element around the outer wall surface of the hollow bodily organ includes displacing tissue anterior to and/or around the guide element by increasing an effective diameter of the guide element.

22. The method of claim 21, wherein increasing the effective diameter of the guide element comprises inflating a balloon.

23. The method of claim 21, wherein increasing the effective diameter of the guide element comprises moving an inner member of the guide element relative to an outer member of the guide element to pivot a dissecting member.

24. The method of claim 21, wherein increasing the effective diameter of the guide element comprises moving an inner member of the guide element relative to an outer member of the guide element to expand a tip diameter of the guide element.

25. The method of claim 9, further comprising placing a conduit guided by the guide element through the wall and out of the hollow bodily organ, wherein directing the guide element comprises moving an inner member of the conduit relative to another member of the conduit so as to flex a tip of the conduit.

26. The method of claim 9, further comprising placing a conduit guided by the guide element through the wall and out of the hollow bodily organ, wherein directing the guide element comprises rotating the conduit relative to the passageway through the wall of the hollow bodily organ.

27. A method of placing an appliance en-around an outer wall surface of a hollow bodily organ, comprising:

entering the hollow bodily organ;

making a passageway through a wall of the hollow bodily organ;

placing the appliance through the passageway to outside the hollow bodily organ, the appliance having an inner lumen extending therethrough;

directing the appliance around the outer wall surface of the hollow bodily organ;

re-entering the hollow bodily organ through the passageway previously made;

adjusting a circumference of the hollow bodily organ by shortening the appliance length around the hollow bodily organ;

affixing the appliance in place; and wherein directing the appliance comprises advancing the appliance over a guide element positioned around the outer wall surface of the hollow bodily organ, the guide element passing through the inner lumen of the appliance.

28. The method of claim 27, further comprising, before placing the appliance through the passageway to outside the hollow bodily organ, advancing the guide element through the passageway to outside the hollow bodily organ, and directing the guide element around the outer wall surface of the hollow bodily organ.

* * * * *